US 6,652,528 B2

(12) United States Patent
Vandewalle (10) Patent No.: US 6,652,528 B2
(45) Date of Patent: Nov. 25, 2003

(54) INTRAMEDULLARY NAIL WITH MODULAR SLEEVE

(75) Inventor: Mark Vandewalle, Pierceton, IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/907,289

(22) Filed: Jul. 17, 2001

(65) Prior Publication Data
US 2003/0018336 A1 Jan. 23, 2003

(51) Int. Cl.[7] .............................................. A61B 17/56
(52) U.S. Cl. ....................................................... 606/62
(58) Field of Search ............................. 606/62, 63, 64, 606/67, 68

(56) References Cited

U.S. PATENT DOCUMENTS

| | | |
|---|---|---|
| 4,805,607 A | 2/1989 | Engelhardt et al. |
| 5,066,296 A | 11/1991 | Chapman et al. |
| 5,112,333 A * | 5/1992 | Fixel ............................ 606/62 |
| 5,122,141 A | 6/1992 | Simpson et al. |
| 5,201,735 A | 4/1993 | Chapman et al. |
| 5,429,640 A | 7/1995 | Shuler et al. |
| 5,489,284 A | 2/1996 | James et al. |
| 5,549,610 A | 8/1996 | Russell et al. |
| 5,569,249 A | 10/1996 | James et al. |
| 5,620,445 A | 4/1997 | Brosnahan et al. |
| 5,626,580 A | 5/1997 | Brosnahan |
| 5,653,709 A | 8/1997 | Frigg |
| 5,658,287 A | 8/1997 | Hofmann et al. |
| 5,855,579 A | 1/1999 | James et al. |
| 6,010,506 A | 1/2000 | Gosney et al. |
| 6,106,528 A | 8/2000 | Durham et al. |
| 6,168,595 B1 | 1/2001 | Durham et al. |
| 6,221,074 B1 | 4/2001 | Cole et al. |

OTHER PUBLICATIONS

Biomet, Inc., Uniflex Femoral Nail Surgical Technique, Warsaw, IN, 1996.
Biomet Inc., Biomet Retrograde Femoral Nail, Warsaw, IN, 1999.

* cited by examiner

Primary Examiner—Eduardo C. Robert
(74) Attorney, Agent, or Firm—Harness, Dickey & Pierce, P.L.C.

(57) ABSTRACT

Long bone fracture fixation systems, and methods for using same, are described. The systems primarily include an intramedullary nail having an elongated throughbore and a first slot for receiving transcortical screws and another slot for receiving an insert. A modular sleeve having a throughbore and a pair of openings for receiving transcortical screws and another pair of dissimilarly shaped openings for receiving the insert are placed over the proximal portion of the intramedullary nail. The modular sleeve can be provided with various opening patterns for receiving transcortical screws at various angles relative to the intramedullary nail. The insert is then properly positioned and is held in place by a hollow set screw disposed within, and coaxial to, the throughbore of the intramedullary nail. In this manner, the throughbore of the intramedullary nail is unobstructed, thus allowing instrumentation to be freely inserted through the entire length of the throughbore.

65 Claims, 8 Drawing Sheets

INTRAMEDULLARY NAIL WITH MODULAR SLEEVE

FIELD OF THE INVENTION

The present invention relates generally to intramedullary nails, and more particularly to a new and improved intramedullary nail system. The system primarily includes an intramedullary nail wherein the proximal portion thereof includes a cavity perpendicular to the longitudinal axis of the nail and an elongated throughbore that is parallel to the longitudinal axis of the nail. A modular sleeve, having a multiplicity of hole patterns formed therein, is received onto the proximal portion of the intramedullary nail. At the distal end of the proximal portion of the intramedullary nail, a fastening assembly is employed to secure the modular sleeve to the proximal portion of the intramedullary nail such that instrumentation may freely pass through the entire length of the elongated throughbore. The fully assembled intramedullary nail system is then able to be secured to the bone tissue with fastener elements capable of being inserted at a variety of different angles through the modular sleeve and the perpendicular cavity.

BACKGROUND OF THE INVENTION

Intramedullary nails are typically used to treat fractures of various long bones, such as diaphyseal fractures of the femur, tibia, and humerus bones. Typically, intramedullary nails are substantially elongated metallic members having one or more cylindrical cavities (typically located in proximal and distal locations) which are perpendicular to the longitudinal axis of the intramedullary nail for receiving a fastener element, such as a transcortical screw. The reason for the presence of the cylindrical cavities is rather simple. Because the intramedullary nails are formed of extremely durable metallic material, e.g., stainless steel, titanium, etc., it is generally undesirable to attempt to drill through this material for obvious reasons. Accordingly, during the manufacturing process of the intramedullary nails, these cylindrical cavities are formed in one or more positions along the length of the intramedullary nails.

The intramedullary nails are positioned within the medullary cavity and can be secured to the proximal and distal fracture segments using transcortical screws which penetrate both cortices of the bone, as well as pass through the cylindrical cavities formed in the intramedullary nail. Thus, unlike Steinmann pins, which can only counteract bending forces, interlocked intramedullary nails can also counteract axial and rotational forces. The interlocked intramedullary nails have a mechanical advantage in comparison to bone plates because the intramedullary nails are implanted centrally within the intramedullary cavity (i.e., the mechanical axis of long bones) rather than placed eccentrically on the surface of the bone.

One problem which has been recognized is that the perpendicular orientation of the cylindrical cavities, relative to the longitudinal axis of the intramedullary nail, severely limits the surgeon's options as to how he or she can fasten the intramedullary nail to the bone tissue with the transcortical screws. Although the perpendicular orientation of the cylindrical cavities is usually acceptable, it is sometimes necessary, due to the site of the fracture, the severity thereof, or the presence of nearby blood vessels and nerves, to place the transcortical screws through the cylindrical cavities in a non-perpendicular orientation relative to the longitudinal axis of the intramedullary nail.

One approach to overcoming this problem can be found in U.S. Pat. No. 5,653,709 to Frigg which discloses a marrow (i.e., intramedullary) nail which includes a nail having a distal end, a proximal end, a longitudinal axis, and a slot in the area of the proximal end, running transverse to the longitudinal axis. A cylindrical casing is provided, which can be slid onto the proximal end of the marrow nail. This casing exhibits a cylindrical axis as well as at least two openings placed at opposite ends of the cylindrical cover. The casing is formed in such a way that upon being slid onto marrow nail, it can be brought into an axial fastening position relative to the nail. Openings are thereby positioned in the fastening position of the casing in the area of the slot and with the latter, the marrow nail and the casing form a transverse channel to admit bone fixation devices.

Although the system disclosed in U.S. Pat. No. 5,653,709 to Frigg appears to provide a means for altering the angles available for the bone fixation devices, e.g., transcortical screws, to be inserted through the slot in the intramedullary nail, it does, however, suffer from a significant deficiency.

Recently, there has been a growing trend towards the use of intramedullary nails which have an elongated throughbore extending centrally along the longitudinal axis of the intramedullary nail so as to permit instrumentation to be inserted into the elongated throughbore, e.g., driver devices for inserting the intramedullary nail into the reamed intramedullary canal.

Because an elongated throughbore is not at all contemplated and solid fixation devices are used, it would be impossible to insert any instrumentation, such as a driver or other devices, inside the center of the intramedullary nail that could extend to, and beyond, the distal end thereof, in the device disclosed in U.S. Pat. No. 5,653,709 to Frigg.

Therefore, there still exists a need for a device for the proximal portion of an intramedullary nail which permits fastener elements, such as transcortical screws, to be inserted through a slot formed in the intramedullary nail at a variety of different angles and orientations relative to the longitudinal axis of the intramedullary nail, while simultaneously permitting instrumentation to be fully and completely received into an elongated throughbore formed along the longitudinal axis of the intramedullary nail even after the device has been secured to the proximal portion of the intramedullary nail.

SUMMARY OF THE INVENTION

In accordance with a first embodiment of the present invention, a fracture fixation system is provided, comprising: (1) an intramedullary nail member having a first area defining a throughbore, wherein the throughbore of the intramedullary nail member is oriented substantially parallel relative to the longitudinal axis of the intramedullary nail member; (2) a sleeve member adapted to be received over the intramedullary nail member, wherein the sleeve member has a first area defining a throughbore, wherein the throughbore of the sleeve member is oriented substantially parallel relative to the longitudinal axis of the sleeve member; and (3) a securing mechanism for securing the sleeve member to the intramedullary nail member such that the throughbore of the intramedullary nail member proximal to the securing mechanism is substantially unobstructed.

In accordance with a second embodiment of the present invention, a fracture fixation system is provided, comprising: (1) an intramedullary nail member including a first area defining a throughbore, wherein the throughbore of the intramedullary nail member is oriented substantially parallel relative to the longitudinal axis of the intramedullary nail member, wherein the intramedullary nail member includes a second area defining an opening which extends completely through at least a portion of the throughbore of the intramedullary nail; (2) a sleeve member adapted to be received over the intramedullary nail member, wherein the sleeve member includes a first area defining a throughbore, wherein the throughbore of the sleeve member is oriented substantially parallel relative to the longitudinal axis of the sleeve member, wherein the sleeve member includes a second area defining an opening which extends completely through at least a portion of the throughbore of the sleeve member; (3) an insert member including an area defining a throughbore, wherein the insert member is capable of being received in the opening of the intramedullary nail member and the opening of the sleeve member so as to substantially align the throughbore of the intramedullary nail member and the throughbore of the insert member; and (4) a fastening member for fastening the intramedullary nail member to the insert member so as to secure the sleeve member to the intramedullary nail member such that the throughbore of the intramedullary nail member is substantially unobstructed.

In accordance with a third embodiment of the present invention, a fracture fixation system is provided, comprising: (1) a substantially cylindrical intramedullary nail member including a first area defining a throughbore, wherein the throughbore of the intramedullary nail member is oriented substantially parallel relative to the longitudinal axis of the intramedullary nail member, wherein the intramedullary nail member includes a second area defining an opening which extends completely through at least a portion of the throughbore of the intramedullary nail, wherein the intramedullary nail member includes a third area defining a second opening which extends completely through at least a portion of the throughbore for receiving a transcortical screw; (2) a substantially cylindrical sleeve member adapted to be received over the intramedullary nail member, wherein the sleeve member includes a first area defining a throughbore, wherein the throughbore of the sleeve member is oriented substantially parallel relative to the longitudinal axis of the sleeve member, wherein the sleeve member includes a second area defining an opening which extends completely through at least a portion of the throughbore of the sleeve member, wherein the sleeve member includes a third area defining a second opening which extends completely through at least a portion of the throughbore for receiving a transcortical screw; (3) an insert member including an area defining a throughbore, wherein the insert member is capable of being received in the opening of the intramedullary nail member and the opening of the sleeve member so as to substantially align the throughbore of the intramedullary nail member and the throughbore of the insert member; and (4) a fastening member for fastening the intramedullary nail member to the insert member so as to secure the sleeve member to the intramedullary nail member such that the throughbore of the intramedullary nail member is substantially unobstructed.

In accordance with a fourth embodiment of the present invention, a method for long bone fracture fixation is provided, comprising: (1) providing a long bone fracture fixation system, including: (a) an intramedullary nail member having a first area defining a throughbore, wherein the throughbore of the intramedullary nail member is oriented substantially parallel relative to the longitudinal axis of the intramedullary nail member; (b) a sleeve member adapted to be received over the intramedullary nail member, wherein the sleeve member has a first area defining a throughbore, wherein the throughbore of the sleeve member is oriented substantially parallel relative to the longitudinal axis of the sleeve member; and (c) a securing mechanism for securing the sleeve member to the intramedullary nail member such that the throughbore of the intramedullary nail member proximal to the securing mechanism is substantially unobstructed; (2) inserting the long bone fracture fixation system into an intramedullary canal; and (3) securing the long bone fracture fixation system in the intramedullary canal with a least one transcortical screw.

In accordance with a fifth embodiment of the present invention, a method for long bone fracture fixation is provided, comprising: (1) providing a long bone fracture fixation system, including: (a) an intramedullary nail member including a first area defining a throughbore, wherein the throughbore of the intramedullary nail member is oriented substantially parallel relative to the longitudinal axis of the intramedullary nail member, wherein the intramedullary nail member includes a second area defining an opening which extends completely through at least a portion of the throughbore of the intramedullary nail; (b) a sleeve member adapted to be received over the intramedullary nail member, wherein the sleeve member includes a first area defining a throughbore, wherein the throughbore of the sleeve member is oriented substantially parallel relative to the longitudinal axis of the sleeve member, wherein the sleeve member includes a second area defining an opening which extends completely through at least a portion of the throughbore of the sleeve member; (c) an insert member including an area defining a throughbore; and (d) a fastening member for fastening the intramedullary nail member to the insert member so as to secure the sleeve member to the intramedullary nail member such that the throughbore of the intramedullary nail member is substantially unobstructed; (2) inserting the long bone fracture fixation system into an intramedullary canal; and (3) securing the long bone fracture fixation system in the intramedullary canal with a least one transcortical screw.

In accordance with a sixth embodiment of the present invention, a method for long bone fracture fixation is provided, comprising: (1) providing a long bone fracture fixation system, including: (a) a substantially cylindrical intramedullary nail member including a first area defining a throughbore, wherein the throughbore of the intramedullary nail member is oriented substantially parallel relative to the longitudinal axis of the intramedullary nail member, wherein the intramedullary nail member includes a second area defining an opening which extends completely through at least a portion of the throughbore of the intramedullary nail, wherein the intramedullary nail member includes a third area defining a second opening which extends completely through at least a portion of the throughbore for receiving a transcortical screw; (b) a substantially cylindrical sleeve member adapted to be received over the intramedullary nail member, wherein the sleeve member includes a first area defining a throughbore, wherein the throughbore of the sleeve member is oriented substantially parallel relative to the longitudinal axis of the sleeve member, wherein the sleeve member includes a second area defining an opening which extends completely through at least a portion of the throughbore of the sleeve member, wherein the sleeve member includes a third area defining a second opening which extends completely through at least a portion of the throughbore for receiving a transcortical screw; (c) an insert member including an area defining a throughbore, wherein the insert member is capable of being received in the opening of the intramedullary nail member and the opening of the sleeve member so as to substantially align the throughbore of the intramedullary nail member and the throughbore of the insert member; and (d) a fastening member for fastening the intramedullary nail member to the insert member so as to secure the sleeve member to the intramedullary nail member such that the throughbore of the intramedullary nail member is substantially unobstructed; (2) inserting the long bone fracture fixation system into an intramedullary canal; and (3) securing the long bone fracture fixation system in the intramedullary canal with a least one transcortical screw.

A more complete appreciation of the present invention and its scope can be obtained from the following detailed description of the invention and the appended claims.

BRIEF DESCRIPTION OF THE DRAWINGS

The present invention will become more fully understood from the detailed description and the accompanying drawings, wherein.

The same reference numerals refer to the same parts throughout the various Figures.

DETAILED DESCRIPTION OF THE INVENTION

Although the present invention is directed primarily towards a long bone fracture fixation system, and methods for using same, it should be understood that the present invention can be practiced on any type of bone that has an intramedullary nail or like device inserted into the intramedullary cavity and which needs to be secured or fastened to the bone itself.

The long bone fracture fixation system of the present invention primarily includes an intramedullary nail, a modular sleeve, a nail key, a set screw, an assembly screw driver, and optionally, a key driver and guide tip.

Figures 1, 2, 3:
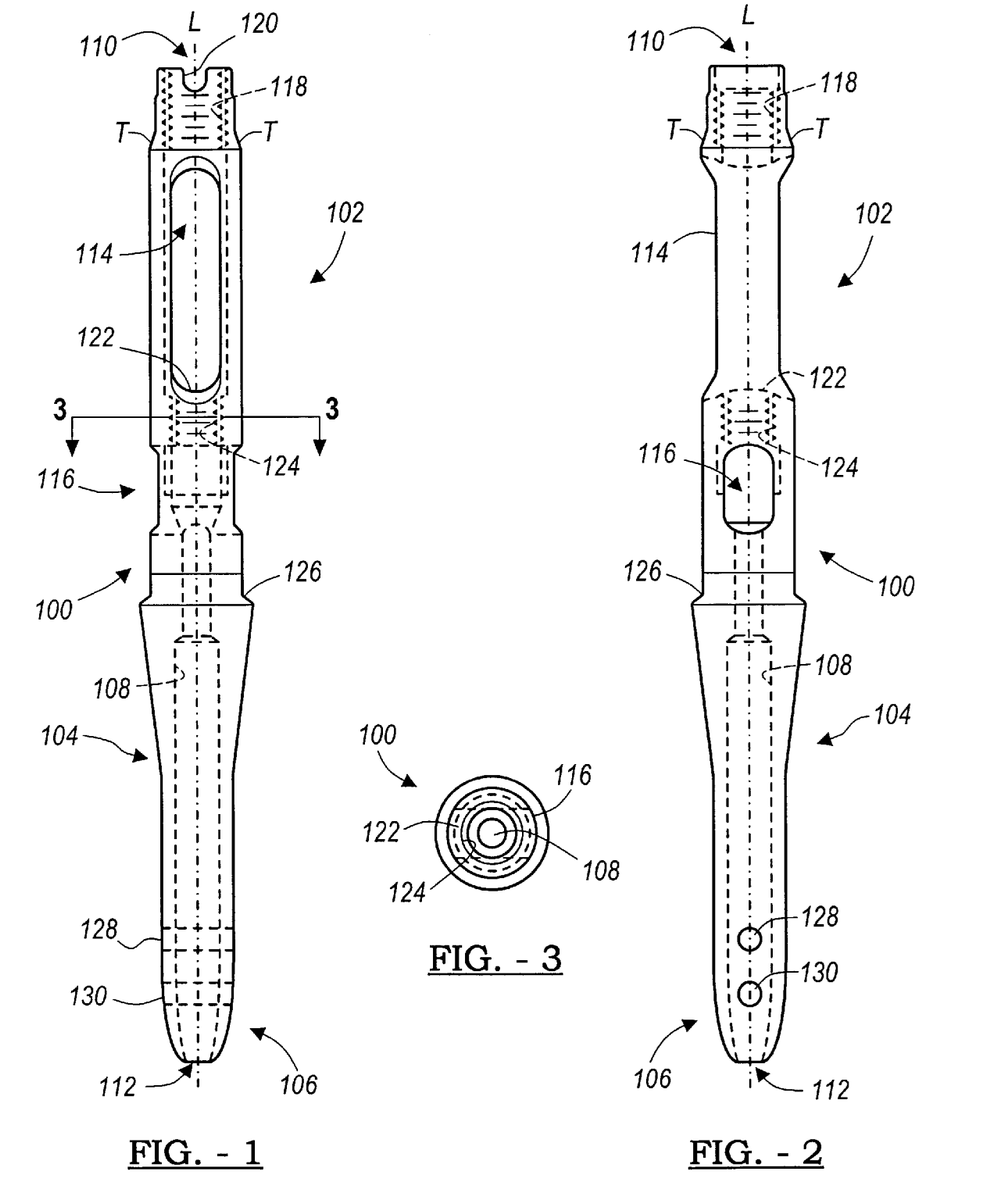
FIG. 1 illustrates a front elevational view of an intramedullary nail of a long bone fracture fixation system, in accordance with one embodiment of the present invention.
FIG. 2 illustrates a side elevational view of the intramedullary nail depicted in FIG. 1, in accordance with one embodiment of the present invention.
FIG. 3 illustrates a cross-sectional view taken along line 3—3 of FIG. 1, in accordance with one embodiment of the present invention.
Figure 4:
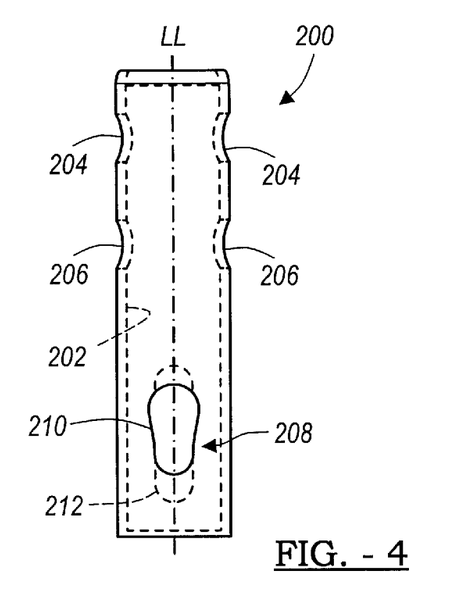
FIG. 4 illustrates a front elevational view of a modular sleeve of a long bone fracture fixation system, in accordance with one embodiment of the present invention.
Figure 5:
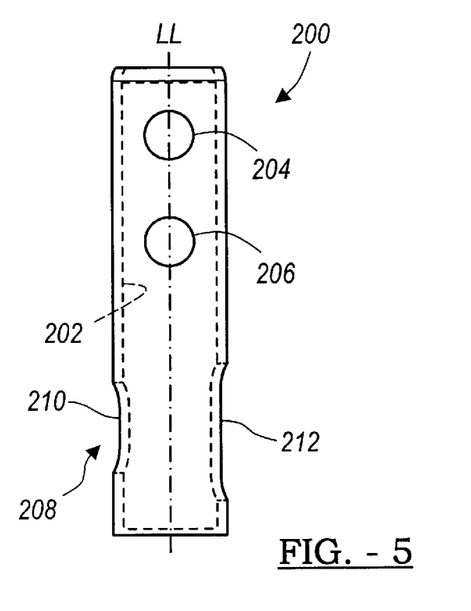
FIG. 5 illustrates a side elevational view of the modular sleeve depicted in FIG. 4, in accordance with one embodiment of the present invention.
Figure 6:
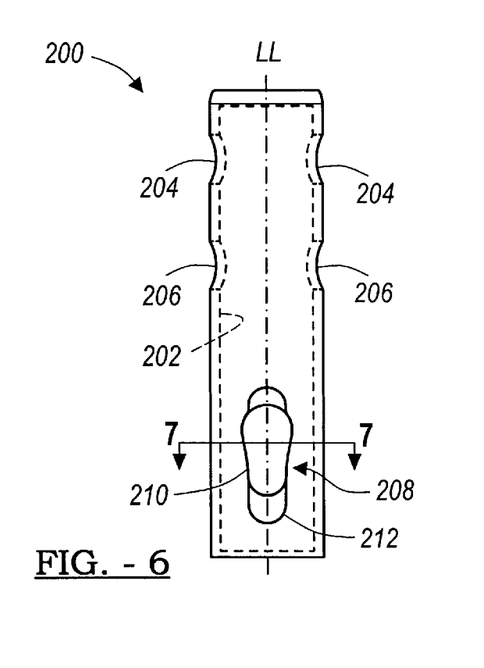
FIG. 6 illustrates a rear elevational view of the modular sleeve depicted in FIG. 4, in accordance with one embodiment of the present invention.
Figure 7:
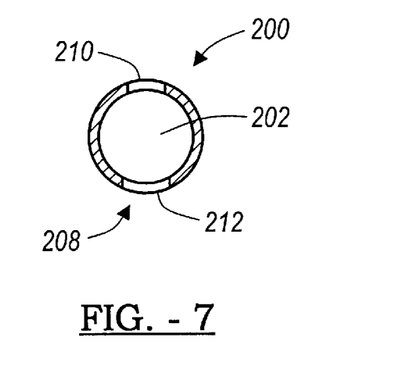
FIG. 7 illustrates a cross-sectional view taken along line 7—7 of FIG. 6, in accordance with one embodiment of the present invention.
Figure 8:
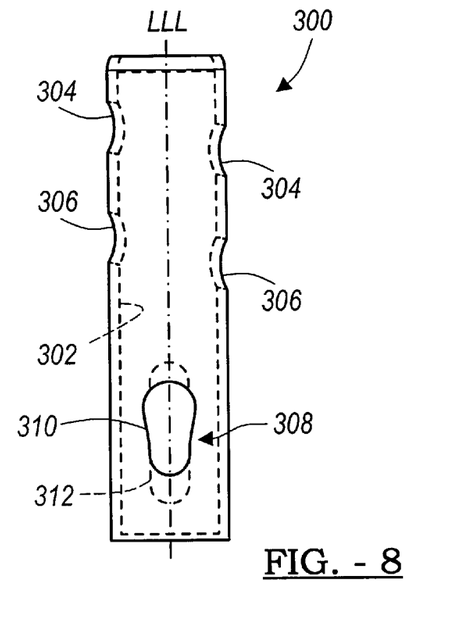
FIG. 8 illustrates a front elevational view of a first alternative modular sleeve of a long bone fracture fixation system, in accordance with an alternative embodiment of the present invention.
Figure 9:
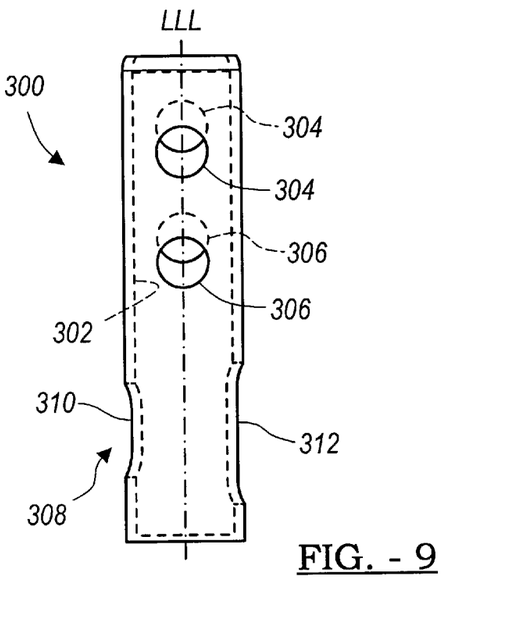
FIG. 9 illustrates a side elevational view of the first alternative modular sleeve depicted in FIG. 8, in accordance with an alternative embodiment of the present invention.
Figure 10:
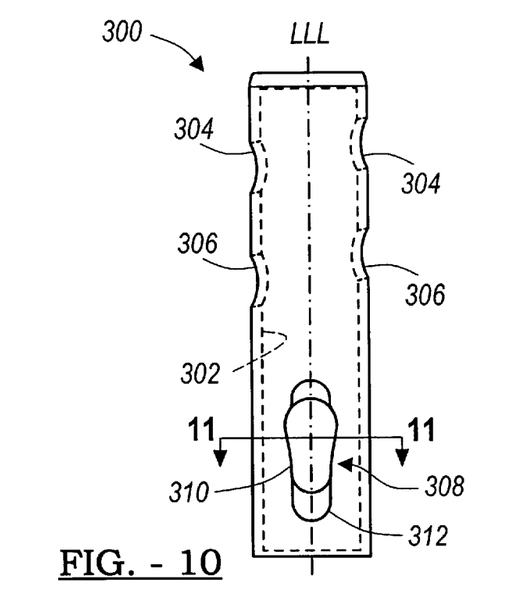
FIG. 10 illustrates a rear elevational view of the first alternative modular sleeve depicted in FIG. 8, in accordance with an alternative embodiment of the present invention.
Figure 11:
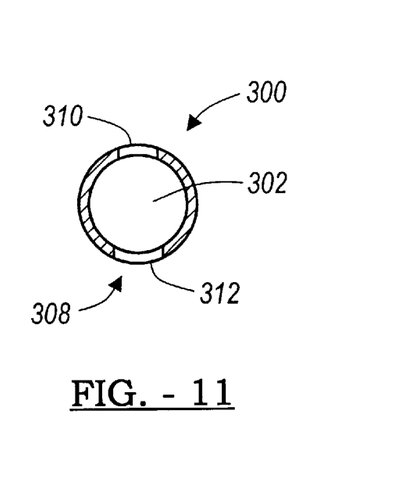
FIG. 11 illustrates a cross-sectional view taken along line 11—11 of FIG. 10, in accordance with an alternative embodiment of the present invention.
Figure 12:
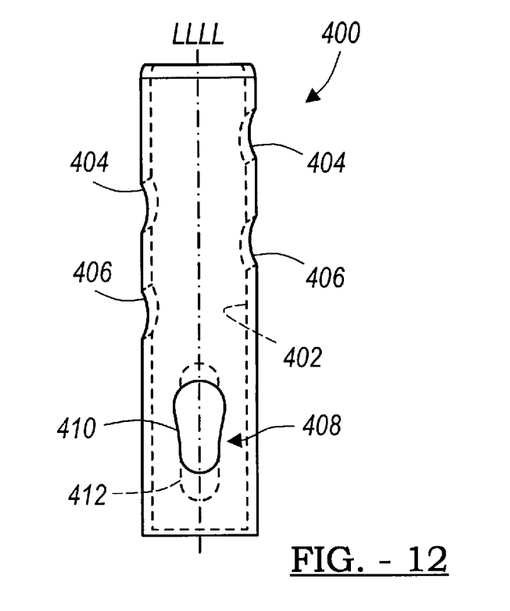
FIG. 12 illustrates a front elevational view of a second alternative modular sleeve of a long bone fracture fixation system, in accordance with a second alternative embodiment of the present invention.
Figure 13:
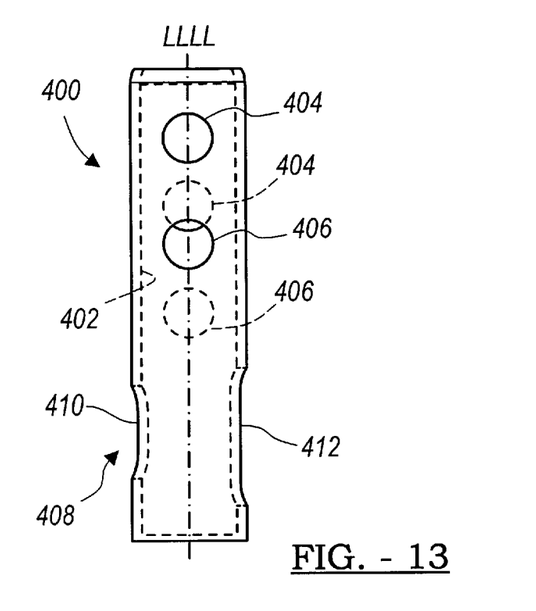
FIG. 13 illustrates a side elevational view of the second alternative modular sleeve depicted in FIG. 12, in accordance with a second alternative embodiment of the present invention.
Figure 14:
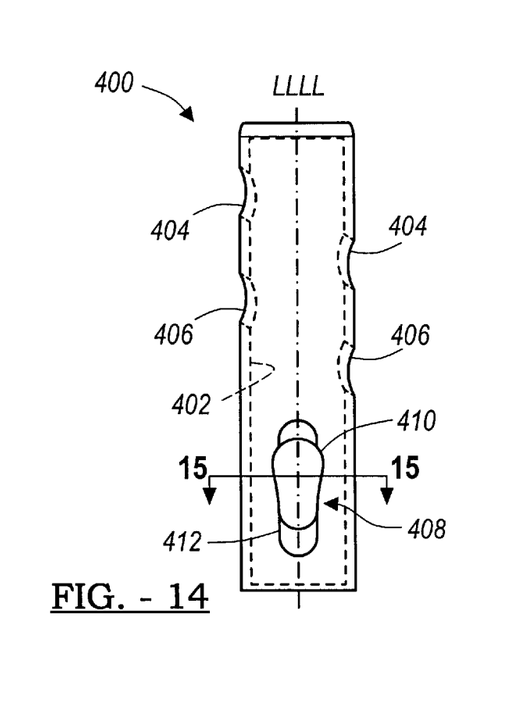
FIG. 14 illustrates a rear elevational view of the second alternative modular sleeve depicted in FIG. 12, in accordance with a second alternative embodiment of the present invention.
Figure 15:
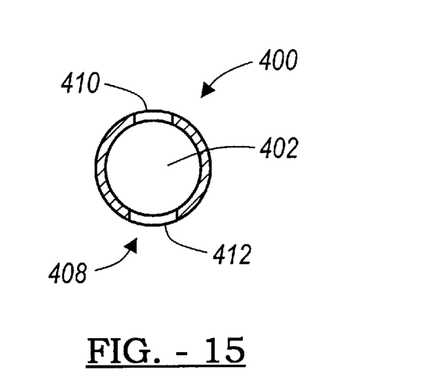
FIG. 15 illustrates a cross-sectional view taken along line 15—15 of FIG. 14, in accordance with a second alternative embodiment of the present invention.
Figures 16, 17:
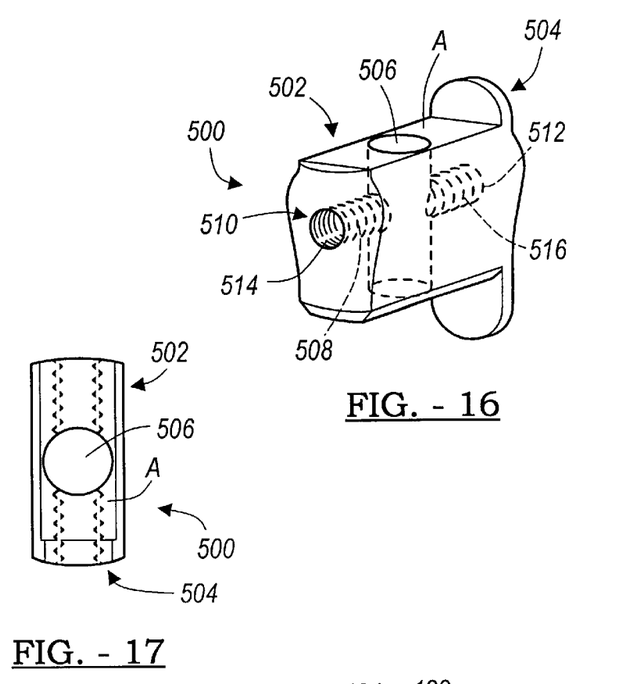
FIG. 16 illustrates a perspective view of a nail key, in accordance with one embodiment of the present invention.
FIG. 17 illustrates a front elevational view of a nail key, in accordance with one embodiment of the present invention.
Figure 18:
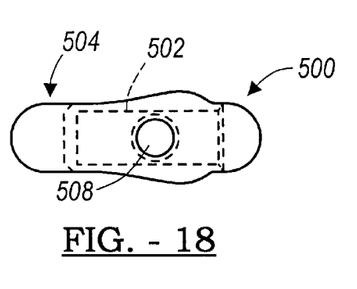
FIG. 18 illustrates a top plan view of a nail key, in accordance with one embodiment of the present invention.
Figure 19:
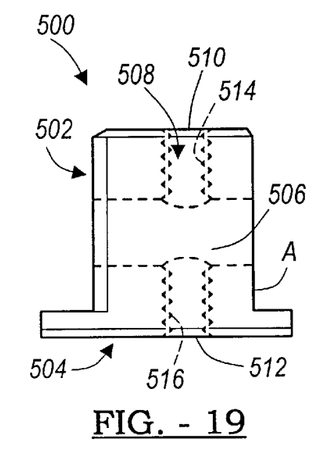
FIG. 19 illustrates a side elevational view of a nail key, in accordance with one embodiment of the present invention.

Referring to FIGS. 1–3, there is shown an exemplary intramedullary nail 100 of a long bone fracture fixation system, in accordance with one embodiment of the present invention. Although the intramedullary nail 100 is shown as being fully cannulated, it should be appreciated that the present invention envisions the use of partially cannulated intramedullary nails as well.

The intramedullary nail 100 includes a proximal portion 102, an intermediate portion 104, and a distal portion 106. The intramedullary nail 100 is not drawn exactly to scale, and in practice would most probably be more elongated than shown in these views to treat long bone fractures. Additionally, portions of the intramedullary nail 100 may also be curved.

The intramedullary nail 100 has an area defining a throughbore 108 formed centrally along it's longitudinal axis L. The throughbore 108 extends from the proximal end 110 all the way to the distal end 112. The throughbore 108, among other things, allows instrumentation to be inserted therethrough, in order to access the distal portion 106 and distal end 112 regions of the intramedullary nail 100.

The proximal portion 102, which has a decreased cross-sectional diameter as compared to the intermediate portion 104, for example, includes an area defining a slot 114 which extends completely across a portion of the throughbore 108. The purpose of the slot 114 and the decreased cross-sectional diameter will be described herein.

Below the slot 114 is another area defining a sleeve 116 which also extends completely across a portion of the throughbore 108. Although the orientation of the sleeve 116 is shown as being positioned 90 degrees from the orientation of the slot 114, it is envisioned that the sleeve 116 may be oriented at any number of positions relative to the slot 114. The purpose of the sleeve 116 will be described herein.

Above the sleeve 116 is a tapered region T which generally denoted the interface between the proximal portion 102 and the intermediate portion 104. The purpose of the tapered region T will be described herein.

The interior surface of the proximal end 110 preferably includes a threaded surface 118 (e.g., for cooperation with an optional cap member, not shown) and an optional notch 120 (e.g., for cooperation with driving and drill guide instrumentation, not shown).

Below the lower surface 122 of the slot 114 there is a threaded surface 124 extending towards the area of the sleeve 116. The purpose of the threaded surface 124 will be described herein.

At the distal end of the proximal portion 102, there is an annular shoulder 126 formed thereon, the purpose of which will be described herein.

At the distal portion 106, there are several optional throughbores 128, 130, respectively, optionally formed at various angles relative to the longitudinal axis L of the intramedullary nail 100, in order to receive fastening members such as transcortical screws (not shown).

In order to provide the orthopedic surgeon a variety of options when deciding how best fix the proximal portions of long bone fractures, the present invention provides a modular sleeve 200, as shown in FIGS. 4–7, in accordance with one embodiment of the present invention.

Preferably, the internal surface of the upper portion of the sleeve 200 is tapered in order to engage the tapered region T of the intramedullary nail 100. By providing a taper to the sleeve 200, it also provides the added benefit of only permitting the sleeve to be placed over the intramedullary nail 100 in only one correct direction or orientation. Additionally, the cross-sectional diameter of the sleeve 200 is larger than the cross-sectional diameter of the proximal portion 102 of the intramedullary nail 100. Thus, when the sleeve 200 is placed over the proximal portion 102 of the intramedullary nail 100, there is an ample amount of clearance space between the two respective surfaces to prevent the generation of wear debris and the occurrence of fretting.

The modular sleeve 200 is a substantially cylindrical and hollow member having an area defining a throughbore 202 extending along it's longitudinal axis LL. Bisecting the throughbore 202 are a series of apertures which extend completely across the throughbore 202.

The first set of apertures include a pair of openings 204, 206, respectively, which are substantially aligned with their matching and substantially identically shaped opening on the opposite side of the modular sleeve 200 so as to present an angle of 0 degrees relative to the longitudinal axis LL of the modular sleeve 200. Although a pair of openings are shown, it is envisioned that either less than or more than this number can be used to practice the present invention. The pair of openings 204, 206, respectively, are intended to receive fastening members, such as transcortical screws (not shown).

Below the pair of the openings 204, 206, respectively, is another opening defining a key seat 208, in that one side of the key seat 208 defines a first keyed sleeve opening 210 and the opposite side of the key seat 208 defines a second keyed sleeve opening 212 that is substantially aligned with the first keyed sleeve opening 210, but has a slightly different shape, the purpose of which will be described herein.

The modular sleeve 200 is intended to be placed over the proximal portion 102 of the intramedullary nail 100 so as to substantially align the pair of the openings 204, 206, respectively, with the slot 114 of the intramedullary nail 100, and to substantially align the key seat 210 with the sleeve 116 of the intramedullary nail 100.

Accordingly, fastening members, such as transcortical screws (not shown) can be simultaneously placed through the pair of openings 204, 206, respectively, and the slot 114, in order to fix the proximal area of a long bone fracture.

Because the modular sleeve 200 has the pair of the openings 204, 206, respectively, oriented as shown, transcortical screws can only be inserted into bone tissue at a substantially perpendicular orientation relative to the longitudinal axis L of the intramedullary nail 100. Occasionally, it is necessary to vary the angle at which the transcortical screws are inserted into the bone tissue, such as to fix a slightly transverse fracture of the proximal femur.

Accordingly, the present invention provides an alternative modular sleeve 300, as shown in FIGS. 8–11, in accordance with an alternative embodiment of the present invention.

The modular sleeve 300 is a substantially cylindrical and hollow member having an area defining a throughbore 302 extending along it's longitudinal axis LLL. Bisecting the throughbore 302 are a series of apertures which extend completely across the throughbore 302.

The first set of apertures include a pair of openings 304, 306, respectively, which are slightly angularly aligned with their matching and substantially identically shaped opening on the opposite side of the modular sleeve 300 so as to present an angle of 15 degrees relative to the longitudinal axis LLL of the modular sleeve 300. Although a pair of openings are shown, it is envisioned that either less than or more than this number can be used to practice the present invention. The pair of openings 304, 306, respectively, are intended to receive fastening members, such as transcortical screws (not shown).

Below the pair of the openings 304, 306, respectively, is another opening defining a key seat 308, in that one side of the key seat 308 defines a first keyed sleeve opening 310 and the opposite side of the key seat 308 defines a second keyed sleeve opening 312 that is substantially aligned with the first keyed sleeve opening 310, but has a slightly different shape, the purpose of which will be described herein.

The modular sleeve 300 is intended to be placed over the proximal portion 102 of the intramedullary nail 100 so as to substantially align the pair of the openings 304, 306, respectively, with the slot 114 of the intramedullary nail 100, and to substantially align the key seat 310 with the sleeve 116 of the intramedullary nail 100.

Accordingly, fastening members, such as transcortical screws (not shown) can be simultaneously placed through the pair of openings 304, 306, respectively, and the slot 114, in order to fix the proximal area of a long bone fracture.

Because the modular sleeve 300 has the pair of the openings 304, 306, respectively, oriented as shown, transcortical screws can only be inserted into bone tissue at a slightly acute orientation (i.e., 15 degrees) relative to the longitudinal axis L of the intramedullary nail 100. Occasionally, it is necessary to further vary the angle at which the transcortical screws are inserted into the bone tissue, such as to fix a fracture of the distal portion of the femur head.

Accordingly, the present invention provides a second alternative modular sleeve 400, as shown in FIGS. 12–15, in accordance with a second alternative embodiment of the present invention.

The modular sleeve 400 is a substantially cylindrical and hollow member having an area defining a throughbore 402 extending along it's longitudinal axis LLLL. Bisecting the throughbore 402 are a series of apertures which extend completely across the throughbore 402.

The first set of apertures include a pair of openings 404, 406, respectively, which are angularly aligned with their matching and substantially identically shaped opening on the opposite side of the modular sleeve 400 so as to present an angle of 35 degrees relative to the longitudinal axis LLLL of the modular sleeve 400. Although a pair of openings are shown, it is envisioned that either less than or more than this number can be used to practice the present invention. The pair of openings 404, 406, respectively, are intended to receive fastening members, such as transcortical screws (not shown).

Below the pair of the openings 404, 406, respectively, is another opening defining a key seat 408, in that one side of the key seat 408 defines a first keyed sleeve opening 410 and the opposite side of the key seat 408 defines a second keyed sleeve opening 412 that is substantially aligned with the first keyed sleeve opening 410, but has a slightly different shape, the purpose of which will be described herein.

The modular sleeve 400 is intended to be placed over the proximal portion 102 of the intramedullary nail 100 so as to substantially align the pair of the openings 404, 406, respectively, with the slot 114 of the intramedullary nail 100, and to substantially align the key seat 410 with the sleeve 116 of the intramedullary nail 100.

Accordingly, fastening members, such as transcortical screws (not shown) can be simultaneously placed through the pair of openings 404, 406, respectively, and the slot 114, in order to fix the proximal area of a long bone fracture.

Thus, with only the need to stock three modular sleeves 200, 300, and 400, respectively, the orthopedic surgeon has the option of addressing a proximal fracture of a long bone in a number of different ways in an efficient and cost-effective manner without resorting to stocking a myriad of intramedullary nails, each having a different transcortical screw hole pattern.

In order to secure the respective modular sleeves to the proximal portion 102 of the intramedullary nail 100, while simultaneously permitting the throughbore 108 of the intramedullary nail 100 to remain unobstructed to permit instrumentation to be easily passed therethrough, the present invention provides a nail key 500, as shown in FIGS. 16–20, in accordance with one embodiment of the present invention.

The nail key 500 is a substantially T-shaped member including a body portion 502, including surface A, and a shelf portion 504. The body portion 502 is intended to be received into the sleeve 116 of the intramedullary nail 100, whereas the shelf portion 504 is intended to be received into the space created between the larger of the keyed sleeves and the outer surface of the intramedullary nail 100, and to be substantially flush with the outer surface of the modular sleeve 200, 300, or 400, respectively. The reason the first keyed sleeve opening 410 is different in shape from the second keyed sleeve opening 412 is that it provides an easy method for properly inserting the nail key 500 in the proper direction and orientation in the sleeve 116. Additionally, at least one of the keyed sleeve openings are preferably provided with a shape (e.g., ovoid) so as to prevent rotation of the nail key 500 once it has been inserted into the sleeve 116. Furthermore, the body portion 502 is preferably tapered to engage the tapered geometry of the respective keyed sleeve opening.

The body portion 502 includes a first throughbore 506 which preferably bisects an optional second throughbore 508. Preferably, both ends 510, 512 of throughbore 508 are provided with a threaded surface 514, 516, respectively. The threaded surfaces 514, 516, respectively, may be of differing cross-sectional diameters and/or thread pitches, the purpose of which will be described herein.

Figure 20:
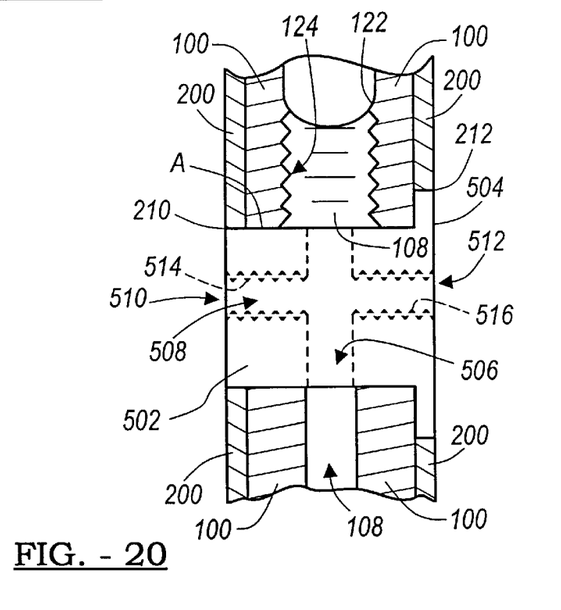
FIG. 20 illustrates a partial cross-sectional view of nail key in cooperation with a modular sleeve and an intramedullary nail, in accordance with one embodiment of the present invention.

By way of a non-limiting example, modular sleeve 200 is placed onto the proximal portion 102 of the intramedullary nail 100. The nail key 500 is then placed initially through the larger keyed sleeve opening 212, then through sleeve 116 and finally terminates flush at the surface of smaller keyed sleeve opening 210. In this manner, throughbore 506 of the nail key 500 is substantially aligned with throughbore 108 of the intramedullary nail 100, so as to avoid the placement of any obstruction in the path of throughbore 108.

Before discussing the methodology of securing the nail key 500 in place, there are several optional instruments that may be used to facilitate the proper positioning and handling of the nail key 500.

Figure 21:
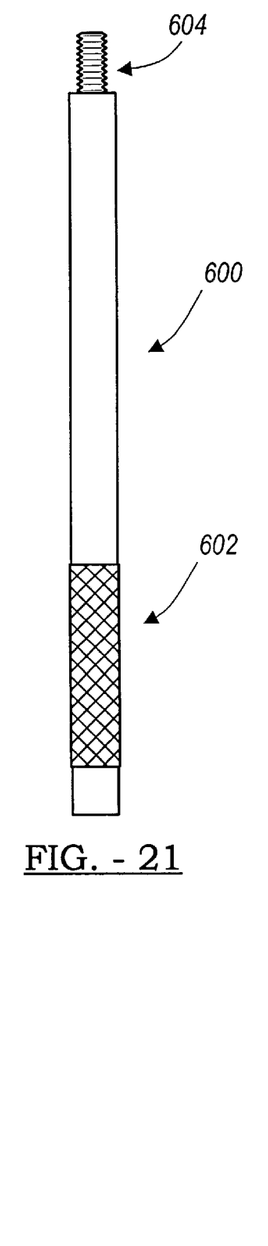
FIG. 21 illustrates a front elevational view of a key driver, in accordance with one embodiment of the present invention.
Figure 22:
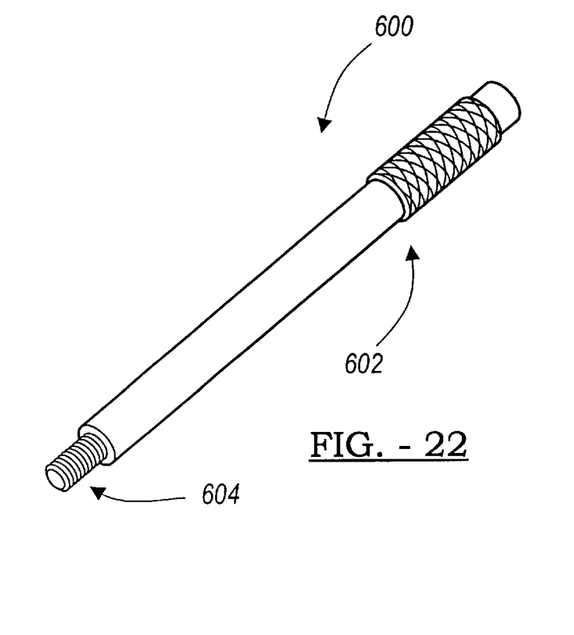
FIG. 22 illustrates a perspective view the key driver depicted in FIG. 21, in accordance with one embodiment of the present invention.

Referring to FIGS. 21–22, there is shown an optional key driver 600 which preferably includes a handle portion 602 and a threaded portion 604. The threaded portion 604 is intended to cooperate with the threaded surface 516 of the end portion 512 of throughbore 508 of the nail key 500. As previously mentioned, threaded surface 516 can optionally be provided with a unique cross-sectional diameter and/or thread pitch so that the threaded portion 604 of the key driver 600 can only engage threaded surface 516, as opposed to being able to engage threaded surface 514.

Once the nail key 500 has been secured in place, the key driver 600 is simply unscrewed from the threaded surface 516 of the end portion 512 of throughbore 508 of the nail key 500.

Figure 23:
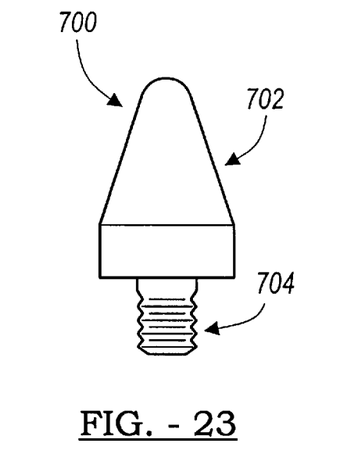
FIG. 23 illustrates a side elevational view of a guide tip, in accordance with one embodiment of the present invention.
Figure 24:
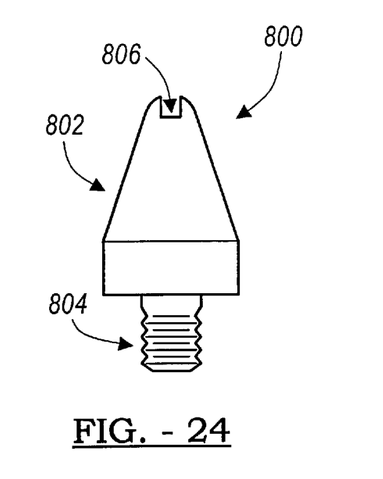
FIG. 24 illustrates a side elevational view of an alternative guide tip, in accordance with one embodiment of the present invention.

Referring to FIGS. 23–24, there is shown two embodiments of an optional guide tip 700, 800, respectively, both of which preferably include a substantially conical tip portion, 702, 802, respectively, and a threaded portion 704, 804, respectively. The threaded portions 704, 804, respectively, are intended to cooperate with the threaded surface 514 of the end portion 510 of throughbore 508 of the nail key 500. Once the nail key 500 has been either properly positioned or secured in place, the guide tip 700, 800, respectively, is simply unscrewed from the threaded surface 514 of the end portion 510 of throughbore 508 of the nail key 500. The only difference between the two guide tips is that guide tip 800 is provided with a notch 806 to allow an optional screwdriver (not shown) to remove the guide tip 800, once the nail key 500 has been secured in place.

Figures 25, 26, 27, 28:
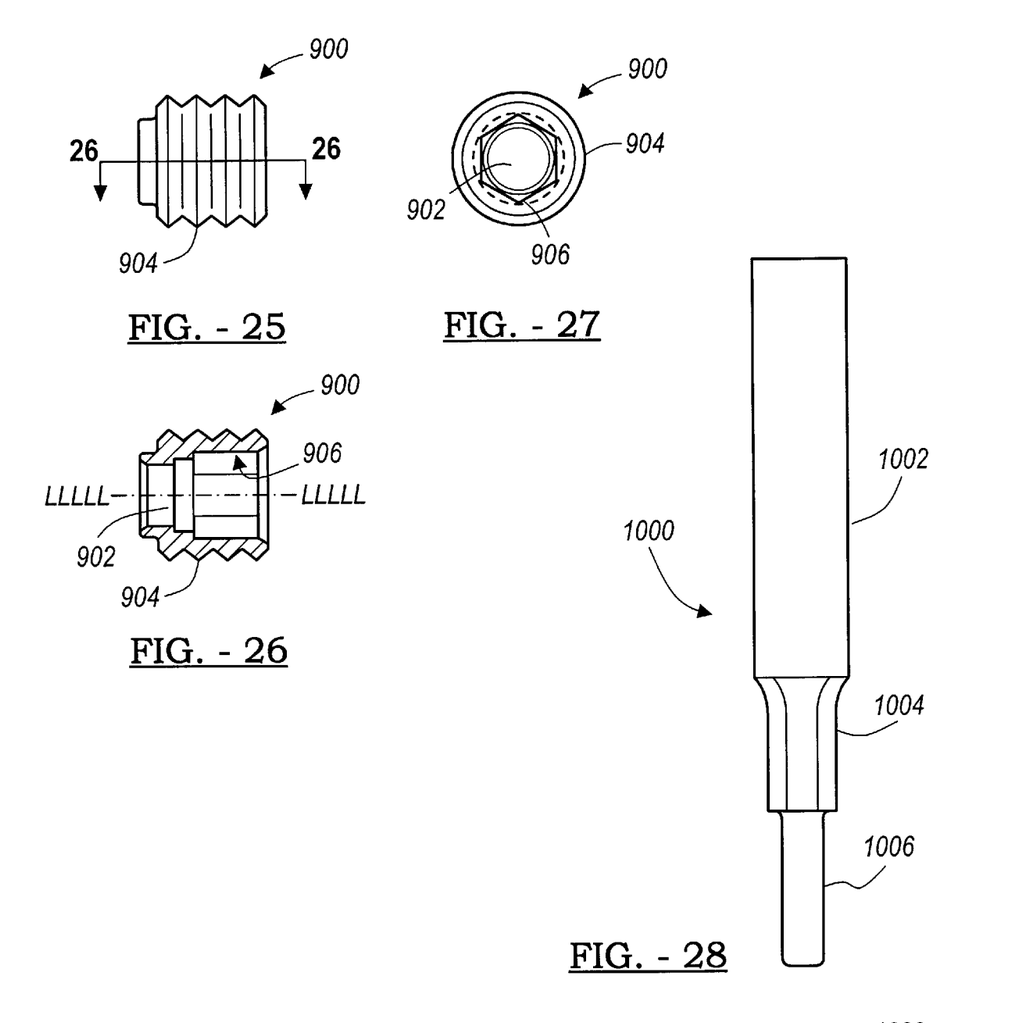
FIG. 25 illustrates a front elevational view of a set screw, in accordance with one embodiment of the present invention.
FIG. 26 illustrates a cross-sectional view taken along line 26—26 of FIG. 25, in accordance with one embodiment of the present invention.
FIG. 27 illustrates a top plan view of the set screw depicted in FIG. 25, in accordance with one embodiment of the present invention.
FIG. 28 illustrates a front elevational view of an assembly screwdriver, in accordance with one embodiment of the present invention.

In order to secure the nail key 500 in place so as to secure the respective modular sleeves to the proximal portion 102 of the intramedullary nail 100, while simultaneously permitting the throughbore 108 of the intramedullary nail 100 to remain unobstructed to permit instrumentation to be easily passed therethrough, the present invention provides a set screw 900, as shown in FIGS. 25–27, in accordance with one embodiment of the present invention.

The set screw 900 is a substantially cylindrical and hollow member having an area defining a throughbore 902 extending along it's longitudinal axis LLLLL. On the outer surface thereof, a threaded surface 904 is provided, and on an inner surface thereof a hex-shaped surface 906 is provided, the reason for both being described herein.

The intended purpose of the set screw 900 is to cooperate with both the threaded surface 124 of the intramedullary nail 100 and surface A of the nail key 500, so as to secure all the primary components of the long bone fixation system of the present invention together. Specifically, the bottom surface of the set screw 900 is intended to bear down upon surface A of the nail key 500.

Because the set screw 900 will be inserted down into a generally inaccessible area of the throughbore 108, it is preferable if a driver device be employed.

Figure 29:
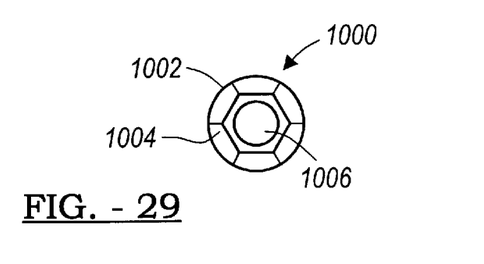
FIG. 29 illustrates a top plan view of the assembly screwdriver depicted in FIG. 28, in accordance with one embodiment of the present invention.

Referring to FIGS. 28–29, there is shown an optional assembly driver 1000 which preferably includes a handle portion 1002, a hex-shaped portion 1004, and a blunt guide portion 1006. The hex-shaped portion 1004 is intended to cooperate with the hex-shaped surface 906 of the set screw 900. Once the set screw 900 has been fully secured to the nail key 500, the assembly driver 1000 is simply lifted upwardly away from the set screw 900.

Figure 30:
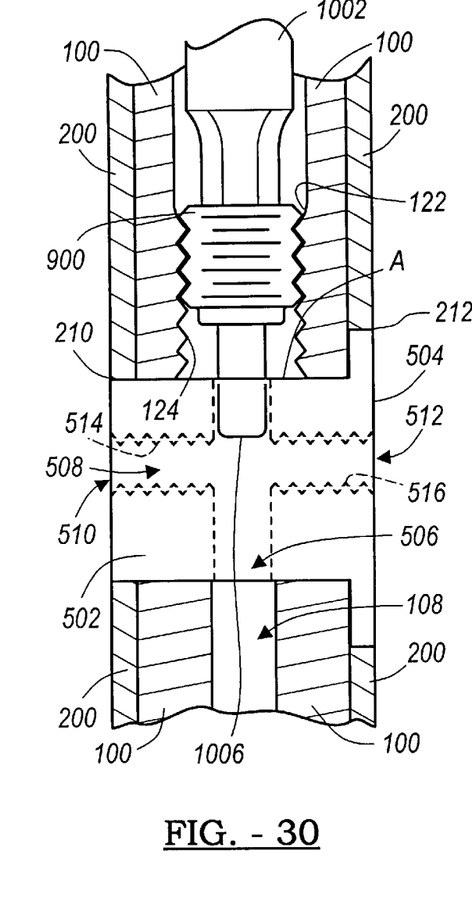
FIG. 30 illustrates a partial cross-sectional view of a set screw being partially inserted into a nail key and intramedullary nail, in accordance with one embodiment of the present invention.
Figure 31:
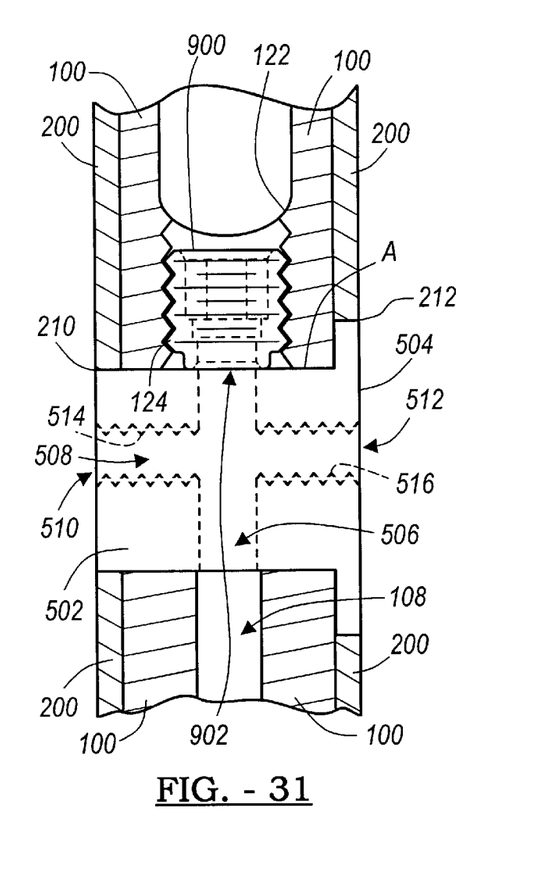
FIG. 31 illustrates a partial cross-sectional view of a set screw being fully inserted into a nail key and intramedullary nail, in accordance with one embodiment of the present invention.

In order to illustrate an example of how the set screw 900 is deployed, reference is made to FIGS. 30–31.

In FIG. 30, set screw 900 is shown as being threaded with the threaded surface 124 of the throughbore 108 as the set screw is being rotated in the appropriate direction by the assembly driver 1000 (only the handle 1002 and the blunt guide portion 1006 are visible in this view).

In FIG. 31, set screw 900 is shown as being fully and properly positioned against the nail key 500 in such a manner as to secure the nail key 500, the modular sleeve 200 (or alternative thereto), and the intramedullary nail 100 together. The set screw 900 may be inserted down into the throughbore 108 against the body portion 502 of the nail key 500, if so desired. However, even though the set screw 900 is inserted coaxial with the throughbore 108 of the intramedullary nail, instrumentation can still freely pass through the throughbore 902 of the set screw 900, and thus through the intermediate and distal portions of the throughbore 108 of the intramedullary nail 100. Additionally, the area around the threaded surface 118 is unobstructed and free to accommodate driving instrumentation or drill guide instrumentation to aid in the insertion of cross screws (e.g., transcortical bone screws) through the respective screw holes on the intramedullary nail 100.

The foregoing description is considered illustrative only of the principles of the invention. Furthermore, because numerous modifications and changes will readily occur to those skilled in the art, it is not desired to limit the invention to the exact construction and process shown as described above. Accordingly, all suitable modifications and equivalents that may be resorted to that fall within the scope of the invention as defined by the claims that follow.

What is claimed is:

1. A long bone fracture fixation system, comprising:
   an intramedullary nail member having a first area defining a throughbore, wherein the throughbore of the intramedullary nail member is oriented substantially parallel relative to the longitudinal axis of the intramedullary nail member, the intramedullary nail member having an outer tapered region located adjacent an end of the intramedullary nail member;
   a sleeve member adapted to be received over the intramedullary nail member, wherein the sleeve member has a first area defining a throughbore, wherein the throughbore of the sleeve member is oriented substantially parallel relative to the longitudinal axis of the sleeve member, the sleeve member having an inner tapered region operable to engage the outer tapered region of the intramedullary nail member to permit the sleeve to be placed over the intramedullary nail member in only one correct direction; and
   a securing mechanism securing the sleeve member to the intramedullary nail member such that the throughbore of the intramedullary nail and the sleeve member are substantially unobstructed, wherein the securing mechanism is oriented substantially parallel relative to the longitudinal axis of the intramedullary nail member and the sleeve member.

2. The system according to claim 1, wherein the intramedullary nail member further includes a second area defining an opening which extends completely through at least a portion of the throughbore for receiving a transcortical screw, and a third area defining a second opening which extends completely through at least a portion of the throughbore of the intramedullary nail.

3. The system according to claim 2, wherein the sleeve member further includes a second area defining an opening which extends completely through at least a portion of the throughbore for receiving a transcortical screw, and a third area defining a second opening which extends completely through at least a portion of the throughbore of the sleeve member.

4. The system according to claim 3, wherein the opening of the sleeve member comprises at least one pair of spaced and opposed areas defining apertures.

5. The system according to claim 4, wherein the at least one pair of spaced and opposed areas defining apertures are substantially aligned with respect to one another.

6. The system according to claim 4, wherein the at least one pair of spaced and opposed areas defining apertures are substantially offset with respect to one another.

7. The system according to claim 1, wherein the intramedullary nail member is substantially cylindrical.

8. The system according to claim 1, wherein the intramedullary nail member includes a first end portion having a decreased cross-sectional diameter.

9. The system according to claim 8, wherein the intramedullary nail member includes a second end portion having an area defining an opening which extends completely through at least a portion of the throughbore for receiving a transcortical screw.

10. The system according to claim 1, wherein at least a portion of a surface of the throughbore of the intramedullary nail member is provided with a threaded surface thereon.

11. The system according to claim 1, wherein the sleeve member is substantially cylindrical.

12. A lone bone fracture fixation system, comprising:
an intramedullary nail member having a first area defining a throughbore, wherein the throughbore of the intramedullary nail member is oriented substantially parallel relative to the longitudinal axis of the intramedullary nail member;
a sleeve member adapted to be received over the intramedullary nail member, wherein the sleeve member has a first area defining a throughbore, wherein the throughbore of the sleeve member is oriented substantially parallel relative to the longitudinal axis of the sleeve member;
a securing mechanism for securing the sleeve member to the intramedullary nail member such that the throughbore of the intramedullary nail member proximal to the securing mechanism is substantially unobstructed, said securing mechanism including,
an insert member having an area defining a throughbore;
wherein the insert member is capable of being received in the intramedullary nail member and the sleeve member so as to substantially align the throughbore of the intramedullary nail member and the throughbore of the insert member; and
a fastening member for fastening the intramedullary nail member to the insert member so as to secure the sleeve member to the intramedullary nail member.

13. The system according to claim 12, wherein the insert member includes a body portion and a flange portion formed on a surface of the body portion, wherein the throughbore extends through the body portion.

14. The system according to claim 13, wherein the flange portion abuts a surface of the intramedullary nail member.

15. The system according to claim 12, wherein at least a portion of a surface of the fastening member is provided with a threaded surface thereon.

16. The system according to claim 15, wherein the threaded surface of the fastening member engages a threaded surface of the throughbore of the intramedullary nail member.

17. The system according to claim 12, further comprising a driver member for facilitating the fastening of the fastening member to the intramedullary nail member.

18. A long bone fracture fixation system, comprising:
an intramedullary nail member including a first area defining a throughbore, wherein the throughbore of the intramedullary nail member is oriented substantially parallel relative to the longitudinal axis of the intramedullary nail member, wherein the intramedullary nail member includes a second area defining an opening which extends completely through at least a portion of the throughbore of the intramedullary nail;
a sleeve member adapted to be received over the intramedullary nail member, wherein the sleeve member includes a first area defining a throughbore, wherein the throughbore of the sleeve member is oriented substantially parallel relative to the longitudinal axis of the sleeve member, wherein the sleeve member includes a second area defining an opening which extends completely through at least a portion of the throughbore of the sleeve member;
an insert member including an area defining a throughbore, wherein the insert member is capable of being received in the opening of the intramedullary nail member and the opening of the sleeve member so as to substantially align the throughbore of the intramedullary nail member and the throughbore of the insert member; and
a fastening member for fastening the intramedullary nail member to the insert member so as to secure the sleeve member to the intramedullary nail member such that the throughbore of the intramedullary nail member is substantially unobstructed.

19. The system according to claim 18, wherein the opening of the intramedullary nail member and the opening of the sleeve member are substantially aligned.

20. The system according to claim 18, wherein the intramedullary nail member further includes a third area defining a second opening which extends completely through at least a portion of the throughbore for receiving a transcortical screw.

21. The system according to claim 18, wherein the intramedullary nail member is substantially cylindrical.

22. The system according to claim 18, wherein the intramedullary nail member includes a proximal portion, an intermediate portion, and a distal portion.

23. The system according to claim 22, wherein the proximal portion includes a proximal end and a distal end.

24. The system according to claim 22, wherein the proximal portion has a decreased cross-sectional diameter compared to the intermediate portion.

25. The system according to claim 22, wherein the proximal portion includes at least one tapered external surface thereon.

26. The system according to claim 25, wherein the sleeve ember engages the at least one tapered external surface of the proximal portion of the intramedullary nail member.

27. The system according to claim 25, wherein the sleeve member further includes a tapered internal surface.

28. The system according to claim 27, wherein the tapered internal surface of the sleeve member engages the at least one tapered external surface of the proximal portion of the intramedullary nail member.

29. The system according to claim 22, wherein the distal portion includes an area defining an opening which extends completely through at least a portion of the throughbore for receiving a transcortical screw.

30. The system according to claim 22, wherein the sleeve member includes a larger cross-sectional diameter than the cross-sectional diameter of the proximal portion of the intramedullary nail member so as to provide a clearance space there between when the sleeve member is brought into engagement with the proximal portion of the intramedullary nail member.

31. The system according to claim 18, wherein the sleeve member is substantially cylindrical.

32. The system according to claim 18, wherein the sleeve member further includes a third area defining a second opening which extends completely through at least a portion of the throughbore for receiving a transcortical screw.

33. The system according to claim 32, wherein the second opening of the sleeve member comprises at least one pair of spaced and opposed areas defining apertures.

34. The system according to claim 33, wherein the at least one pair of spaced and opposed areas defining apertures are substantially aligned with respect to one another.

35. The system according to claim 33, wherein the at least one pair of spaced and opposed areas defining apertures are substantially offset with respect to one another.

36. The system according to claim 18, wherein at least a portion of a surface of the throughbore of the intramedullary nail member is provided with a threaded surface thereon.

37. The system according to claim 18, wherein the insert member includes a body portion and a flange portion formed on a surface of the body portion, wherein the throughbore extends through the body portion.

38. The system according to claim 37, wherein the flange portion abuts a surface of the intramedullary nail member.

39. The system according to claim 18, wherein at least a portion of a surface of the fastening member is provided with a threaded surface thereon.

40. The system according to claim 39, wherein the threaded surface of the fastening member engages the threaded surface of the throughbore of the intramedullary nail member.

41. The system according to claim 18 further comprising a driver member for facilitating the fastening of the fastening member to the intramedullary nail member.

42. A long bone fracture fixation system, comprising:
a substantially cylindrical intramedullary nail member including a first area defining a throughbore, wherein the throughbore of the intramedullary nail member is oriented substantially parallel relative to the longitudinal axis of the intramedullary nail member, wherein the intramedullary nail member includes a second area defining an opening which extends completely through at least a portion of the throughbore of the intramedullary nail, wherein the intramedullary nail member includes a third area defining a second opening which extends completely through at least a portion of the throughbore for receiving a transcortical screw;
a substantially cylindrical sleeve member adapted to be received over the intramedullary nail member, wherein the sleeve member includes a first area defining a throughbore, wherein the throughbore of the sleeve member is oriented substantially parallel relative to the longitudinal axis of the sleeve member, wherein the sleeve member includes a second area defining an opening which extends completely through at least a portion of the throughbore of the sleeve member, wherein the sleeve member includes a third area defining a second opening which extends completely through at least a portion of the throughbore for receiving a transcortical screw;
an insert member including an area defining a throughbore, wherein the insert member is capable of being received in the opening of the intramedullary nail member and the opening of the sleeve member so as to substantially align the throughbore of the intramedullary nail member and the throughbore of the insert member; and
a fastening member for fastening the intramedullary nail member to the insert member so as to secure the sleeve member to the intramedullary nail member such that the throughbore of the intramedullary nail member is substantially unobstructed.

43. The system according to claim 42, wherein the opening of the intramedullary nail member and the opening of the sleeve member are substantially aligned.

44. The system according to claim 42, wherein the intramedullary nail member includes a proximal portion, an intermediate portion, and a distal portion.

45. The system according to claim 44, wherein the proximal portion includes a proximal end and a distal end.

46. The system according to claim 44, wherein the proximal portion has a decreased cross-sectional diameter compared to the inter portion.

47. The system according to claim 46, wherein the sleeve member has a larger cross-sectional diameter than the cross-sectional diameter of the proximal portion of the intramedullary nail member so as to provide a clearance space there between when the sleeve member is brought into engagement with the proximal portion of the intramedullary nail member.

48. The system according to claim 44, wherein the proximal portion includes at least one tapered external surface thereon.

49. The system according to claim 48, wherein the sleeve member engages the at least one tapered external surface of the proximal portion of the intramedullary nail member.

50. The system according to claim 48, wherein the sleeve member further includes a tapered internal surface.

51. The system according to claim 50, wherein the tapered internal surface of the sleeve member engages the at least one tapered external surface of the proximal portion of the intramedullary nail member.

52. The system according to claim 44, wherein the distal portion has an area defining an opening which extends completely through at least a portion of the throughbore for receiving a transcortical screw.

53. The system according to claim 42, wherein the second opening of the sleeve member comprises at least one pair of spaced and opposed areas defining apertures.

54. The system according to claim 53, wherein the at least one pair of spaced and opposed areas defining apertures are substantially aligned with respect to one another.

55. The system according to claim 53, wherein the at least one pair of spaced and opposed areas defining apertures are substantially offset with respect to one another.

56. The system according to claim 42, wherein at least a portion of a surface of the throughbore of the intramedullary nail member is provided with a threaded surface thereon.

57. The system according to claim 42, wherein the insert member includes a body portion and a flange portion formed on a surface of the body portion, wherein the throughbore extends through the body portion.

58. The system according to claim 57, wherein the flange portion abuts a surface of the intramedullary nail member.

59. The system according to claim 42, wherein at least a portion of a surface of the fastening member is provided with a threaded surface thereon.

60. The system according to claim 59, wherein the threaded surface of the fastening member engages the threaded surface of the throughbore of the intramedullary nail member.

61. The system according to claim 42, further comprising a driver member for facilitating the fastening of the fastening member to the intramedullary nail member.

62. A method for long bone fracture fixation, comprising:
providing a long bone fracture fixation system, including:
an intramedullary nail member including a first area defining a throughbore, wherein the throughbore of the intramedullary nail member is oriented substantially parallel relative to the longitudinal axis of the intramedullary nail member, wherein the intramedullary nail member includes a second area defining an opening which extends completely through at least a portion of the throughbore of the intramedullary nail;

a sleeve member adapted to be received over the intramedullary nail member, wherein the sleeve member includes a first area defining a throughbore, wherein the throughbore of the sleeve member is oriented substantially parallel relative to the longitudinal axis of the sleeve member, wherein the sleeve member includes a second area defining an opening which extends completely through at least a portion of the throughbore of the sleeve member;

an insert member including an area defining a throughbore; and a fastening member for fastening the intramedullary nail member to the insert member so as to secure the sleeve member to the intramedullary nail member such that the throughbore of the intramedullary nail member is substantially unobstructed;

inserting the long bone fracture fixation system into an intramedullary canal; and securing the long bone fracture fixation system in the intramedullary canal with a least one transcortical screw.

63. A method for long bone fracture fixation, comprising:

providing a long bone fracture fixation system, including:

a substantially cylindrical intramedullary nail member including a first area defining a throughbore, wherein the throughbore of the intramedullary nail member is oriented substantially parallel relative to the longitudinal axis of the intramedullary nail member, wherein the intramedullary nail member includes a second area defining an opening which extends completely through at least a portion of the throughbore of the intramedullary nail, wherein the intramedullary nail member includes a third area defining a second opening which extends completely through at least a portion of the throughbore for receiving a transcortical screw;

a substantially cylindrical sleeve member adapted to be received over the intramedullary nail member, wherein the sleeve member includes a first area defining a throughbore, wherein the throughbore of the sleeve member is oriented substantially parallel relative to the longitudinal axis of the sleeve member, wherein the sleeve member includes a second area defining an opening which extends completely through at least a portion of the throughbore of the sleeve member, wherein the sleeve member includes a third area defining a second opening which extends completely through at least a portion of the throughbore for receiving a transcortical screw;

an insert member including an area defining a throughbore, wherein the insert member is capable of being received in the opening of the intramedullary nail member and the opening of the sleeve member so as to substantially align the throughbore of the intramedullary nail member and the throughbore of the insert member; and a fastening member for fastening the intramedullary nail member to the insert member so as to secure the sleeve member to the intramedullary nail member such that the throughbore of the intramedullary nail member is substantially unobstructed;

inserting the long bone fracture fixation system into an intramedullary canal; and securing the long bone fracture fixation system in the intramedullary canal with a least one transcortical screw.

64. A bone fracture fixation system, comprising:

an intramedullary nail member defining a throughbore, wherein the throughbore substantially parallel relative to a longitudinal axis of the intramedullary nail member;

a sleeve member adapted to be received over the intramedullary nail member, the sleeve member defining a throughbore, wherein the throughbore of the sleeve member is oriented substantially parallel relative to the longitudinal axis of the sleeve member; and a securing member operable to secure the sleeve member to the intramedullary nail member, said securing member defining a throughbore, wherein upon positioning the securing member transversely through the sleeve member and the intramedullary nail member, the throughbore of the securing member substantially axially aligns with the throughbores of the intramedullary nail member and the sleeve member.

65. The bone fracture fixation system of according to claim 64 wherein said securing member includes a flange that is substantially nestingly received within the sleeve member to provide a substantially flush outer surface.

* * * * *

UNITED STATES PATENT AND TRADEMARK OFFICE
CERTIFICATE OF CORRECTION

PATENT NO.    : 6,652,528 B2
DATED         : November 25, 2003
INVENTOR(S)   : Mark Vandewalle It is certified that error appears in the above-identified patent and that said Letters Patent is hereby corrected as shown below:

Column 4,
Lines 8 and 36, "a" should be -- at --.

Column 5,
Line 9, "a" should be -- at --.

Column 7,
Line 19, "it's" should be -- its --.
Line 61, after "best" insert -- to --.

Column 8,
Lines 13 and 58, "it's" should be -- its --.

Column 9,
Line 38, "it's" should be -- its --.

Column 11,
Line 31, "it's" should be -- its --.

Column 13,
Line 14, "lone" should be -- long --.

Column 14,
Line 40, "ember" should be -- member --.

Column 16,
Line 5, "inter" should be -- intermediate --.

Column 17,
Line 21, "a" should be -- at --.

UNITED STATES PATENT AND TRADEMARK OFFICE
CERTIFICATE OF CORRECTION

PATENT NO. : 6,652,528 B2
DATED : November 25, 2003
INVENTOR(S) : Mark Vandewalle It is certified that error appears in the above-identified patent and that said Letters Patent is hereby corrected as shown below:

Column 18,
Line 21, "a" should be -- at --.
Line 25, after "throughbore" insert -- is --.
Line 42, delete "of".

Signed and Sealed this

Third Day of May, 2005

JON W. DUDAS
*Director of the United States Patent and Trademark Office*